(12) United States Patent
Duineveld et al.

(10) Patent No.: US 8,210,846 B2
(45) Date of Patent: Jul. 3, 2012

(54) BRUSHHEAD ASSEMBLY-HANDLE INTERFACE ARRANGEMENT FOR A DROPLET JET SYSTEM FOR CLEANING TEETH

(75) Inventors: Paulus Cornelis Duineveld, Drachten (NL); Martinus Bernardus Stapelbroek, Rolde (NL); Jasper Zuidervaart, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 351 days.

(21) Appl. No.: 12/303,128

(22) PCT Filed: Jun. 12, 2007

(86) PCT No.: PCT/IB2007/052203
§ 371 (c)(1),
(2), (4) Date: Dec. 2, 2008

(87) PCT Pub. No.: WO2007/144821
PCT Pub. Date: Dec. 21, 2007

(65) Prior Publication Data
US 2009/0317758 A1 Dec. 24, 2009

Related U.S. Application Data

(60) Provisional application No. 60/814,381, filed on Jun. 15, 2006.

(51) Int. Cl.
*A61C 1/10* (2006.01)

(52) U.S. Cl. .......................................... 433/85
(58) Field of Classification Search ............ 433/84–85, 433/137; 137/580
See application file for complete search history.

(56) References Cited

U.S. PATENT DOCUMENTS

| 4,531,913 | A | 7/1985 | Taguchi |
| 4,991,249 | A | 2/1991 | Suroff |
| 5,192,206 | A | 3/1993 | Davis et al. |
| 5,203,698 | A * | 4/1993 | Blake et al. ............... 433/88 |
| 5,765,759 | A * | 6/1998 | Bruns et al. .............. 239/398 |
| 6,322,361 | B1 | 11/2001 | Esrock |
| 2001/0041321 | A1 | 11/2001 | Segal |

FOREIGN PATENT DOCUMENTS

| EP | 0661024 | 7/1995 |
| GB | 2213732 A | 8/1989 |
| GB | 2302285 | 1/1997 |
| WO | 9719755 | 6/1997 |
| WO | 9947067 A1 | 9/1999 |
| WO | 2005070324 | 8/2005 |

* cited by examiner

*Primary Examiner* — Cris L Rodriguez
*Assistant Examiner* — Mirayda A Aponte

(57) ABSTRACT

The interface structure includes a handle portion (12) having separate supply lines for gas and liquid, and a head portion (18) also having separate supply lines for gas and liquid, wherein the upper surface of the handle portion is configured relative to the lower surface of the head portion, with or without a separate locking member, that the gas and liquid lines in the handle connect in a fluid-sealing relationship with the gas and liquid lines in the head as the head portion is operatively positioned on the handle portion.

22 Claims, 19 Drawing Sheets

BRUSHHEAD ASSEMBLY-HANDLE INTERFACE ARRANGEMENT FOR A DROPLET JET SYSTEM FOR CLEANING TEETH

This invention relates generally to gas-assisted droplet jet systems for cleaning teeth, which include separate supply lines for the gas and the droplet liquid, and more specifically concerns an interface structure for removably connecting the head assembly of the system to the handle assembly.

A droplet jet system for cleaning teeth is described in International Publication No. WO2005070324. That system produces a spray of small liquid droplets which are accelerated by a gas flow in a head portion of the system, for cleaning the frontal and interproximal areas of a user's teeth. The system includes a replaceable head portion relative to a permanent handle portion for supply and control of separate gas and liquid lines.

However, there are several important considerations involving the interface for a replaceable head. The interface must include a reliable, effective seal between the gas and liquid lines, respectively, in the head and handle portions, and must be cost-effective as well as convenient and produce an error-proof connection. The interface must be structured so that by a single action, both gas and liquid lines are connected/disconnected. Typically, the interface should hold a pressure of 8 Bar or more.

Accordingly, it is desirable to have an interface which meets the above-desired structural considerations.

Accordingly, the invention includes an interface structure for connecting a handle portion of a droplet jet teeth cleaning system to a head assembly portion, comprising: a handle portion containing a source of liquid from which droplets may be produced in the head portion and a source of gas for accelerating the resulting droplets to a desired velocity, including separate supply lines for liquid and gas in the handle; a head assembly having separate supply lines for liquid and gas and an assembly for accelerating the liquid droplets out of the head using gas from the gas supply line therein, wherein the handle liquid and gas supply lines, respectively, are arranged to align only with the head liquid and gas supply lines when the head is operatively positioned on the handle; and a sealing assembly for sealing the head gas line to the handle gas line and the head liquid line to the handle liquid line when the head portion is operatively positioned on the handle portion, wherein the handle and head portion are so configured, with or without a locking member, that the head and handle portions can be locked together with the respective gas lines and the respective liquid lines being in a sealed relationship and such that as the head portion is positioned onto or removed from the handle portion, the respective liquid lines and gas lines come into registry or are removed therefrom as an automatic result.

Figure 20A:
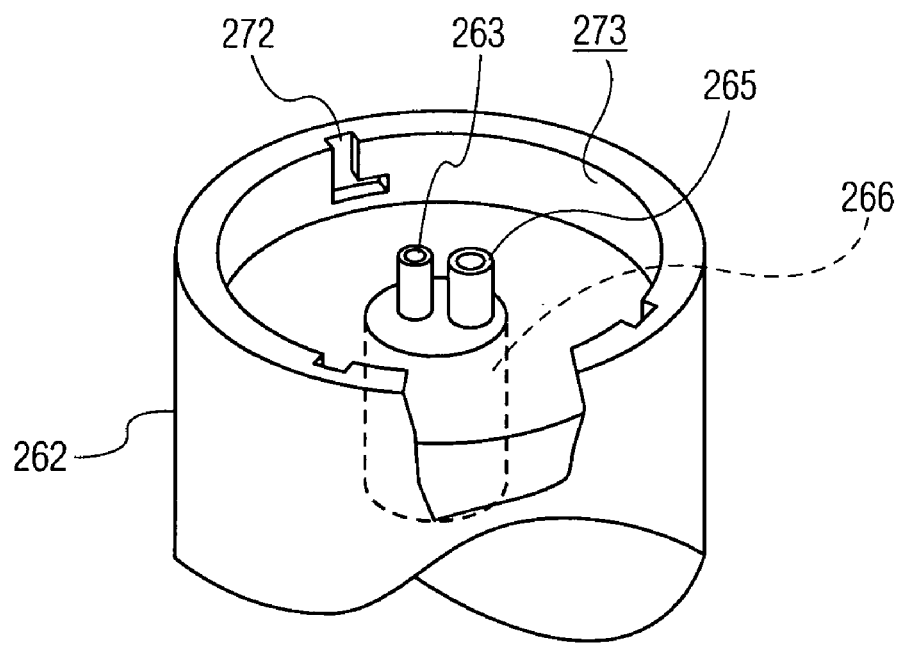
FIGS. 20A and 20B are partially cut-away and cross-sectional views, respectively, of still another embodiment of the interface structure.
Figure 20B:
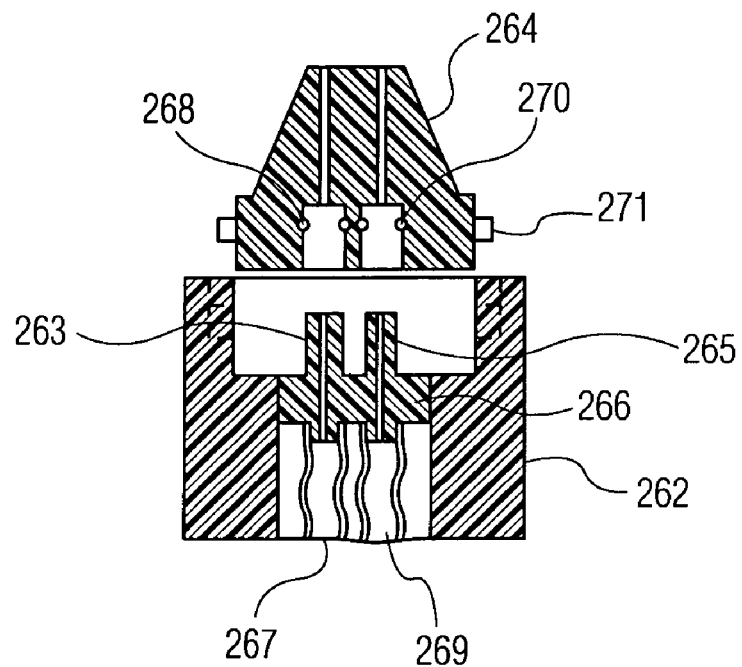
Figure 21:
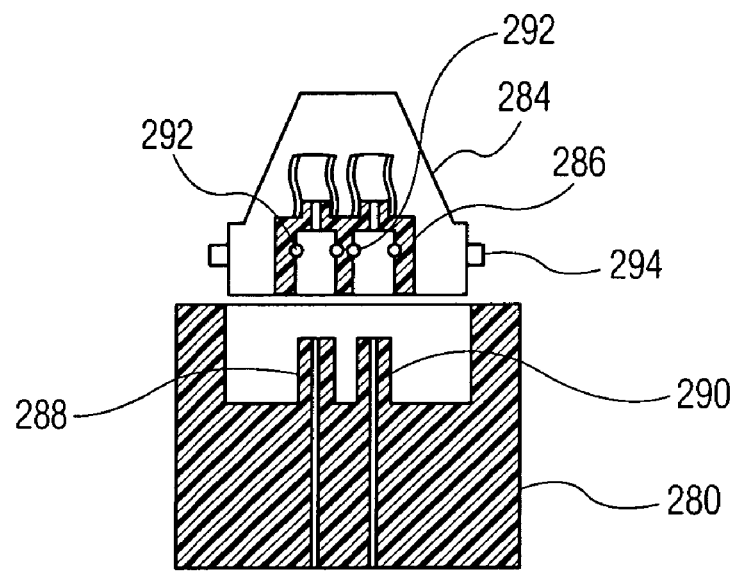

FIG. 21 is a cross-sectional view showing a variation of the interface structure of FIGS. 20A and 20B As discussed briefly above, and in International Publication No. WO2005070324, which is owned by the assignee of the present invention and the contents of which are hereby incorporated by reference, a system for producing a spray of fine liquid droplets by means of a separate supply of pressurized gas, such as air, is known. With such a structure, it is advantageous that a head portion of the article, containing the liquid droplet-generating assembly and the droplet-accelerating assembly, using pressurized gas, accelerate the liquid droplets to advanced speed, and be removable from the handle portion, which contains the liquid and gas sources and the control elements for the system, including the on/off control, as well as any user interface structure.

A physical head/handle interface structure is necessary to enable the head portion to be conveniently and reliably removable from the handle portion and for a new head to be inserted. It is important that the interface structure be arranged so that the head can be positioned on the handle portion in only one orientation, so that the gas line in the handle is always connected to the gas line in the head and the liquid line in the handle is always connected to the liquid line in the head. Further, the arrangement must provide an adequate seal between the respective lines in the head and the handle, and must be simple and safe to use, as well as cost-effective. A single action must produce a reliable connect/disconnect for both lines.

Figure 1A:
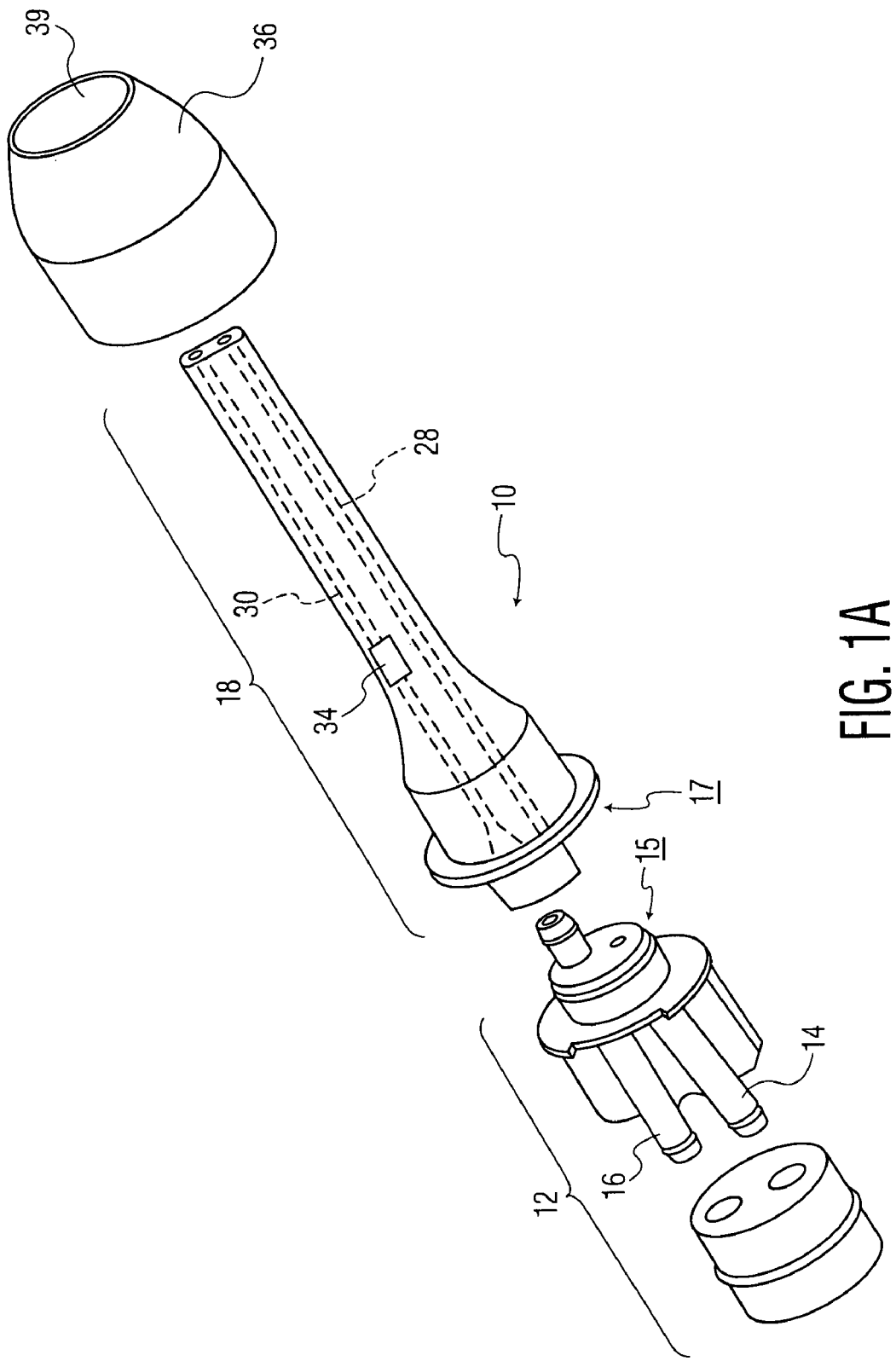
FIGS. 1A and 1B show an exploded view and a partial cross-sectional view of a first interface embodiment between a handle and a head portion of a droplet jet system described herein.
Figure 1B:
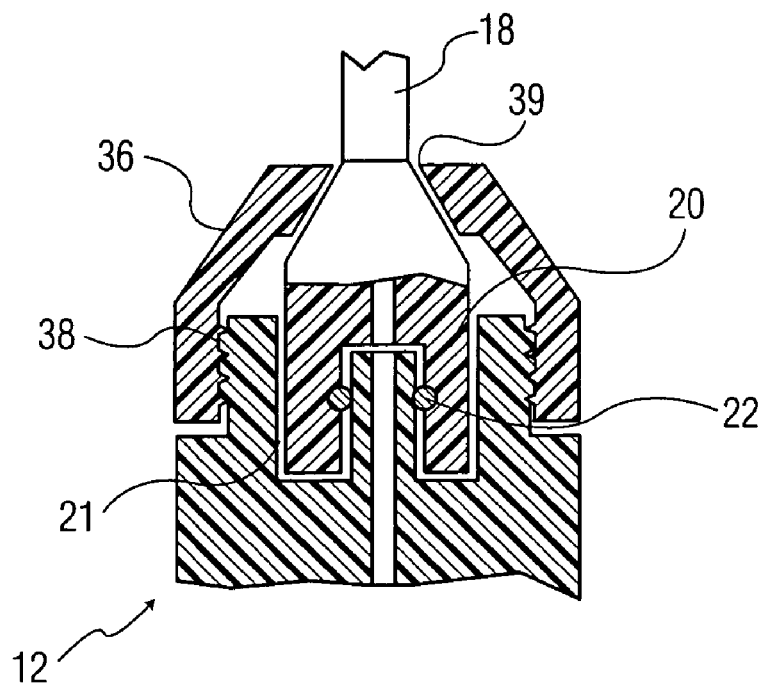

One embodiment of such a structure is shown in FIGS. 1A and 1B. The droplet jet system, shown generally at 10, includes an internal portion of a handle 12 which at the top end includes two separate supply lines, one line 14 for gas and the other line 16 for liquid. As disclosed in the '324 publication, the gas, typically air, is used to accelerate the liquid droplets to the desired speed, which is in the range of 30 70 meters per second in the embodiment described, although the interface structure described herein is not limited to such a droplet velocity.

The droplet jet system 10 also includes a head portion 18 which contains a droplet-generating assembly and droplet acceleration assembly (not specifically shown). The accelerated droplets are directed into the mouth of the user for cleaning of his/her teeth.

The upper surface 15 of the handle portion 12 and the lower surface 17 of the head portion 18 are configured so that they fit snugly together. In the embodiment shown, for each of the gas and liquid connections, respectively, referring to FIG. 1B, the lower surface of the head portion has a donut-like protrusion 20 which fits into a mating cavity 21 in the upper surface 15 of the handle portion. O ring seals 22 are positioned between protrusion 20 and a wall defining cavity 21, providing a fluid-tight connection between the two.

The gas and liquid supply lines 14 and 16 in the handle 12 are configured to be in registry with mating gas and liquid supply lines 28 and 30 in the head portion 18. The respective free ends of the supply lines are configured such that the gas supply line from the handle can only be in registry with and connect with the gas supply line in the head, with the same being true for the liquid supply lines in the handle and head. The liquid supply line in the head may include a filter 34 to trap impurities in the liquid.

The head 18 is locked to the handle 12 by a tall circular ring 36, which is threaded onto a mating portion 38 of the upper surface 15 of the handle. The head portion 18 extends through opening 39 in the ring 36.

To remove head 18 from handle 12, ring 36 is unthreaded from the handle, and the head is then simply lifted away from the handle, with the donut protrusion of the head disengaging from the cavity in the upper surface of the handle. Conversely, a new head is first positioned onto the original handle portion and then the ring 36 is threaded sufficiently to lock or tighten the head onto the handle. The arrangement of FIGS. 1A and 1B provides a reliable and convenient single-action connection (one action connects/disconnects both gas and liquid) between the handle and the head, as well as being safe, fluid-tight and cost-effective.

Figure 2A:
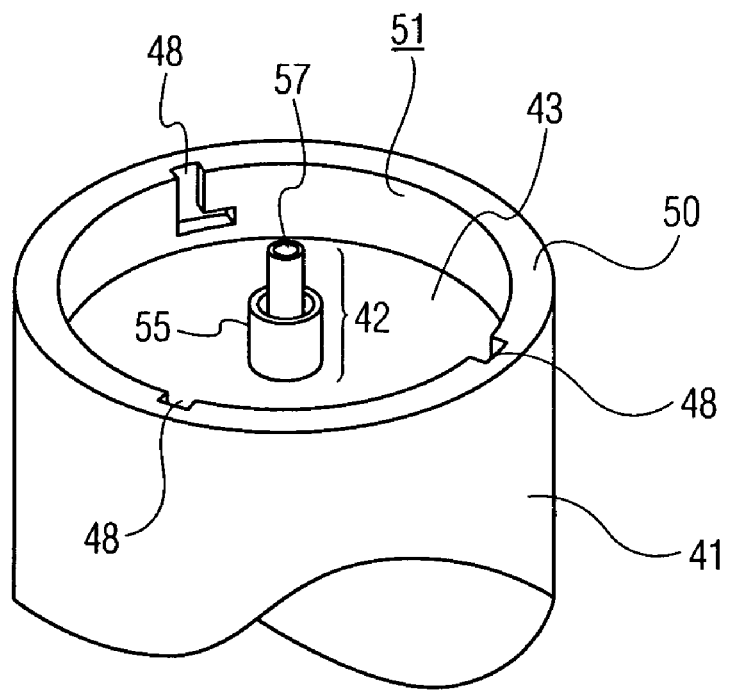
FIGS. 2A and 2B show a schematic view and a cross-sectional view, respectively, of a second embodiment of the interface structure.
Figure 2B:
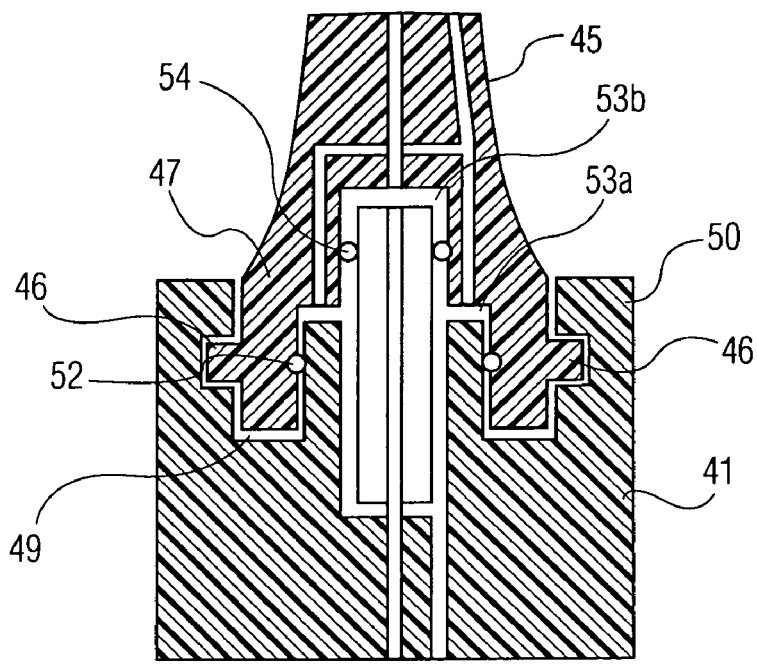

FIGS. 2A and 2B show a different interface structure, in which the fluid and gas flow are coaxial. A coaxial connector element 42 extends from the upper surface 43 of the handle 41, while a head portion 45 includes a mating coaxial connection at the lower surface thereof The lower part 47 of the head portion is configured to fit into a cavity 49 in the upper surface of the handle portion, and includes bayonet protrusion 46 on the outer surface thereof, which mate with similar bayonet slots 48 in the inner surface 51 of handle top wall 50, to provide a locking capability between the head and the handle.

Two O rings 52 and 54 are spaced between the mating portions of the head and the handle, defining a lower chamber 53a to which the outer opening 55 in the coaxial connector opens onto. The outer opening of the coaxial line in the head also opens onto the chamber 53a. The inner opening 57 of the coaxial connector in the handle opens onto an upper chamber 53b defined by O ring 54, as does the inner opening of the coaxial connection in the head 45.

The head 45 is removed by turning it counterclockwise until the protrusions 46 reach the end of the horizontal portion of the bayonet slot then pulling the head away from the handle, with the protrusions moving along the vertical portions of the bayonet slots, which open onto the top edge of the handle top wall 50. To insert the head portion, the protrusions on the head are lined up with the slots in the handle wall 50, pushed together and then rotated clockwise.

Figure 3:
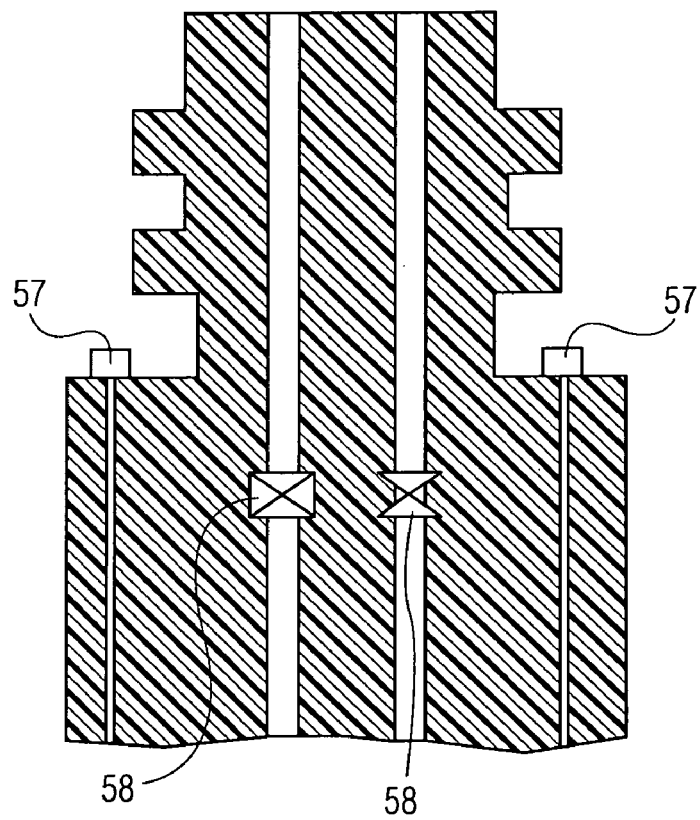
FIG. 3 is a simplified diagram showing a valve and switch arrangement for shutting off the gas and liquid supply lines in the handle when the head is removed from the handle.

It is desirable in the head/handle interfaces disclosed herein that there be a valve and control switch arrangement, by which the liquid and gas are both shut off in the handle when the head portion is removed, in order to prevent leakage or any spray from the lines in the handle portion during that time. FIG. 3 shows a simple electromechanical switch and valve arrangement, by which when the head has separated from the handle, switches 57 activate valves 58, which close off the liquid and the gas lines. The switch itself could be either electrical or mechanical in operation.

Figure 4:
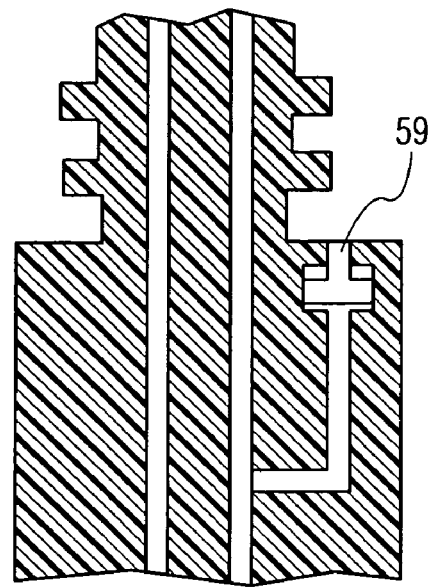
FIG. 4 is a diagram showing a system for locking the head to the handle when the system is pressurized.

FIG. 4 is an alternative arrangement which shows a locking structure to prevent the head from being removed from the handle when the system is pressurized. A cylinder 59 extends into a mating opening in the lower surface of the head when pressure builds up in the gas line.

Figure 5:
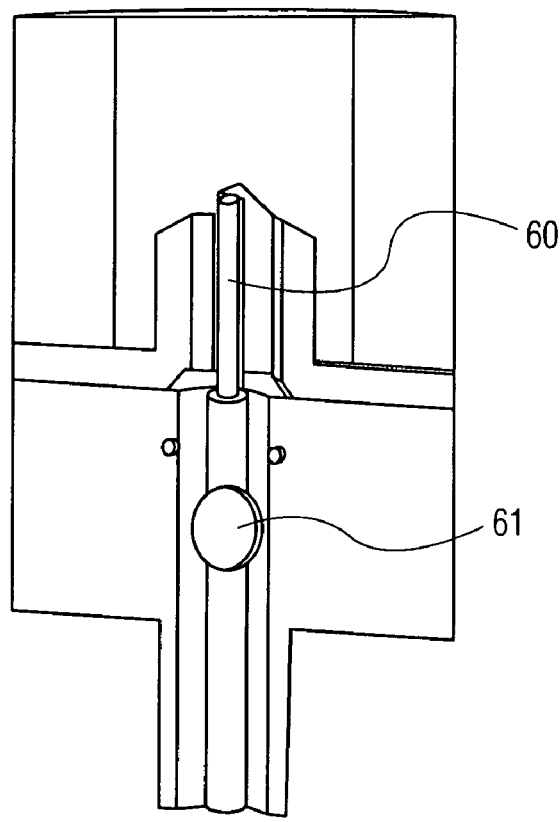
FIG. 5 is a cross-sectional diagram showing a ball and pin arrangement for shutting off the gas and liquid supply lines when the head is removed.

FIG. 5 shows an alternative to the switch/valve shutoff arrangement, involving a ball and pin assembly, in which a pin 60, connected to the head, moves a ball 61, present in the handle, to permit flow in a line when the head is positioned onto the handle. A ball/pin combination is required for each line. When the head is removed, the respective balls move by action of the liquid and the gas to cut off the flows thereof. Other control mechanisms are possible as well.

Figure 6:
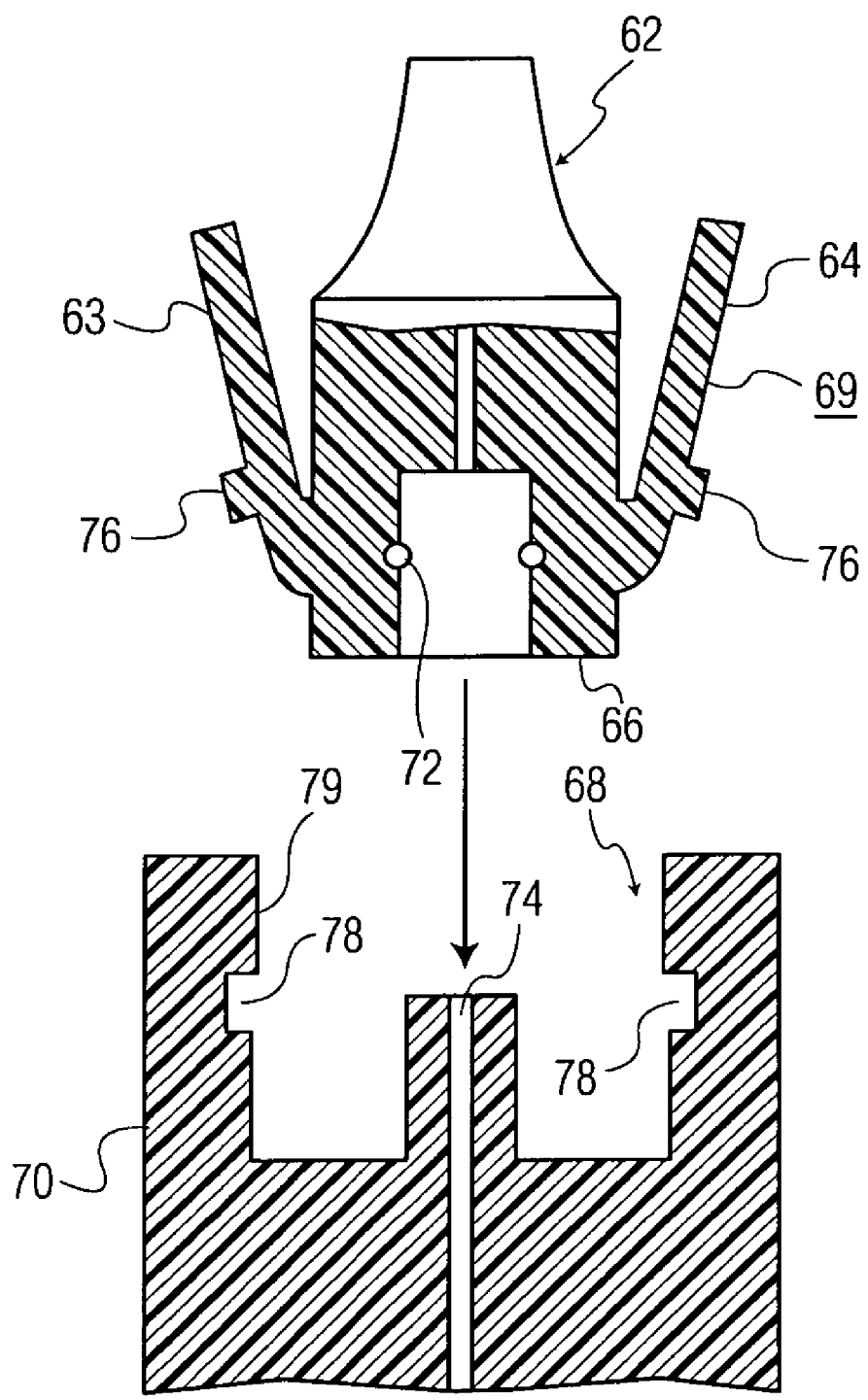
FIG. 6 is a cross-sectional diagram showing another embodiment of the interface structure.

FIG. 6 shows another interface embodiment in which a head portion 62 includes two opposing elastic members 63, 64 extending from the outer surface thereof. The lower surface 66 of head 62 is configured to fit with the upper surface 68 of handle portion 70. A fluid-tight relationship is created between the head and handle by O ring 72. For simplicity, only one supply line 74 is illustrated in the head and handle; however, it should be understood that the head and handle each have both gas and liquid lines.

The outer surface 69 of elastic members 63, 64 include protrusions 76 which mate with matching cavities 78 in the inner surface of wall 79 of handle 70. When the head is to be removed from the handle, the user pinches the elastic members inwardly, removing protrusions 76 from mating cavities 78, permitting the head to be lifted easily away from the handle. A new head can be simply positioned on the handle by pushing the head down onto the handle, forcing the elastic members inwardly, until the protrusions 76 come into registry with cavities 78, at which point the members 63, 64 spring outwardly, with protrusions 76 mating with cavities 78, locking the head to the handle.

Figure 7:
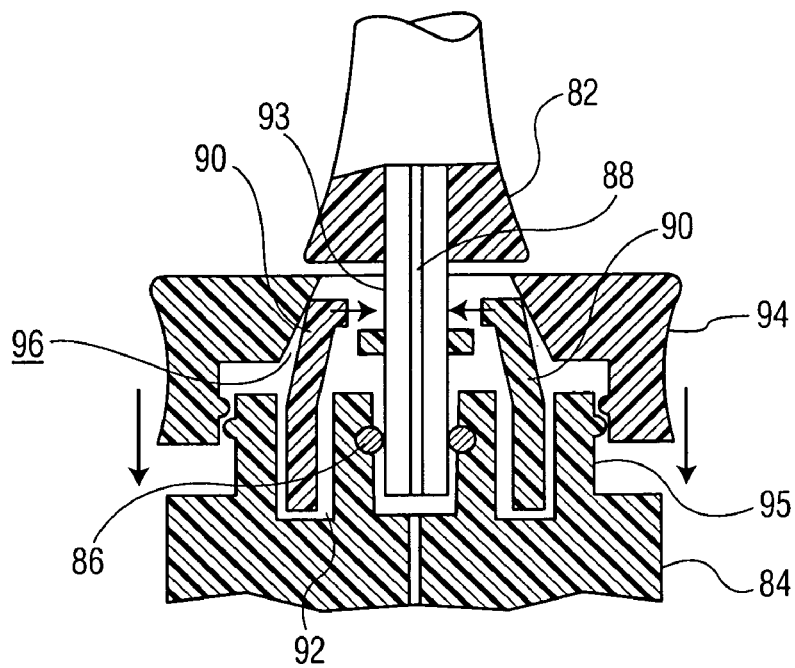
FIG. 7 is a cross-sectional diagram showing another embodiment of the interface structure.

FIG. 7 shows a somewhat more complex interface arrangement, involving a head portion 82, a handle portion 84 and an O ring seal 86. Again, for simplicity of illustration, only one handle/head fluid line 88 is illustrated. A plurality of elastic leg members 90 are positioned in a cavity 92, spaced around the periphery of the upper surface of the handle, with a ring member 94 threaded onto an exterior portion 95 of the upper surface of handle 84. An inner surface 96 of ring member 94 mates with elastic legs 90, such that as ring 94 is threaded down onto the handle, the upper portions of legs 90 are forced inwardly against a lower extending portion 93 of head portion 84, thus capturing and locking head 82 to the handle 84. When the head is to be removed, ring 94 is simply unscrewed, which releases legs 90, permitting head 82 to be simply pulled away from the handle 84.

Figure 8A:
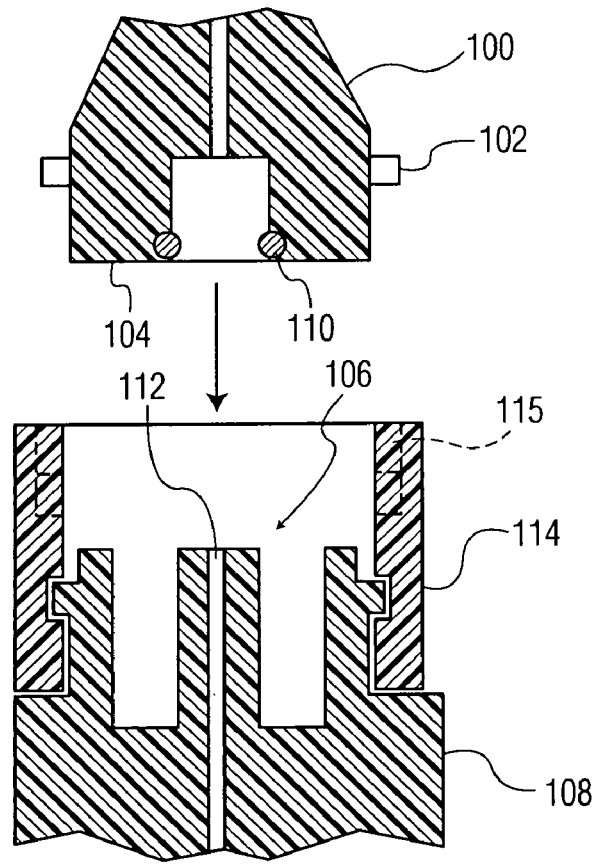
FIGS. 8A and 8B are schematic and cross-sectional diagrams, respectively, showing another embodiment of the interface structure.
Figure 8B:
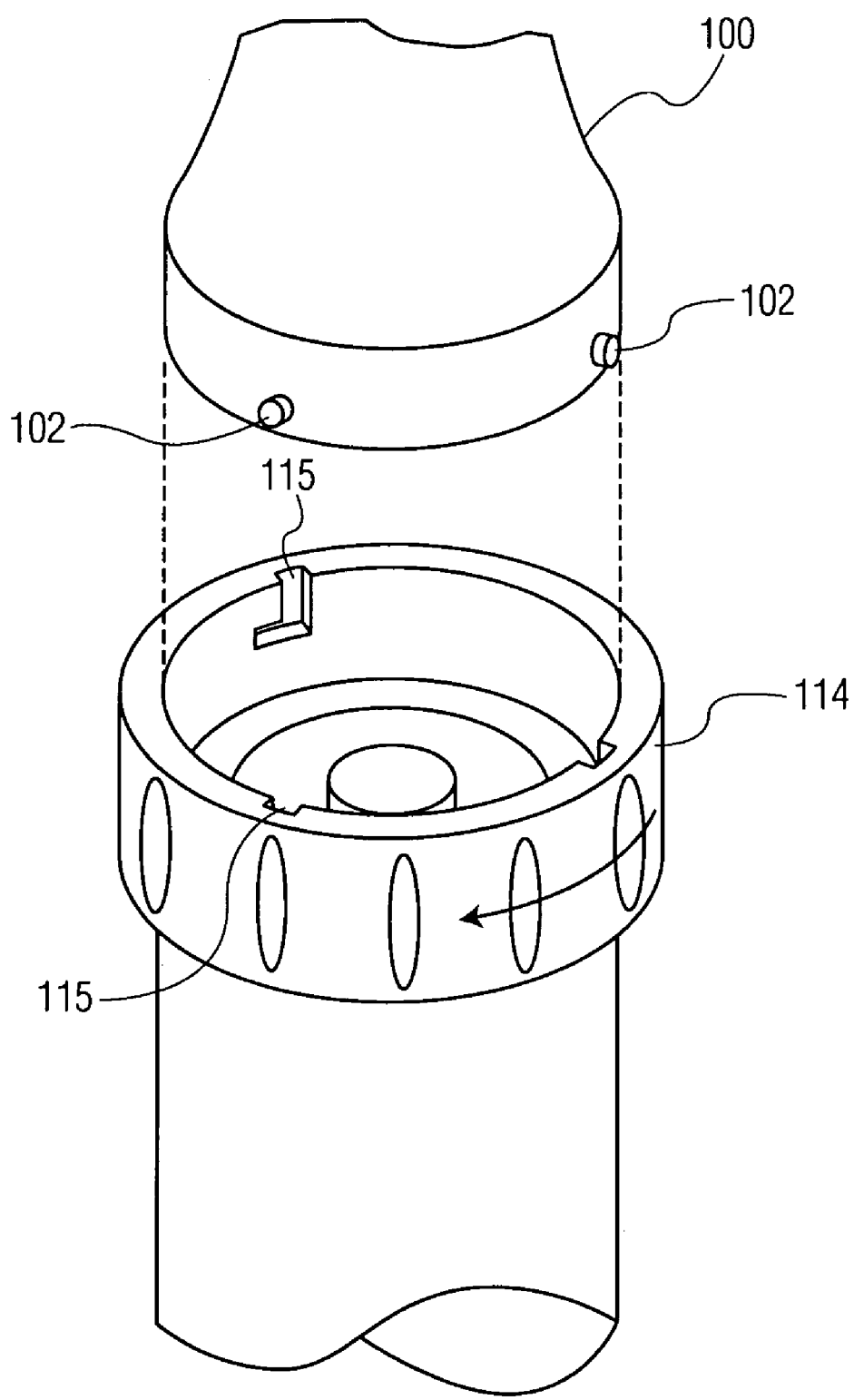
Figure 9A:
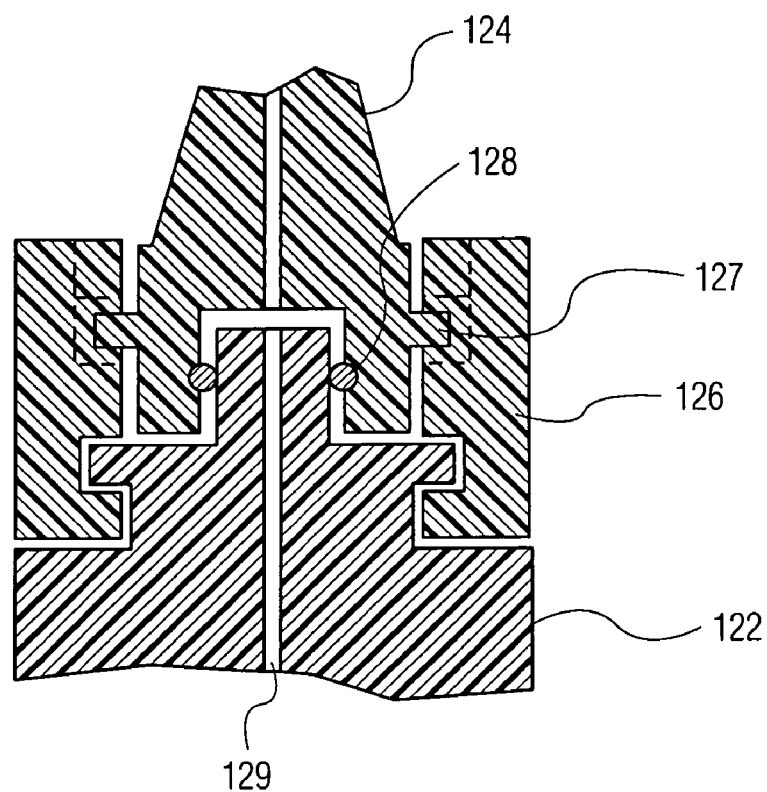
FIG. 9A is a cross-sectional diagram of a further embodiment of the interface structure.
Figure 9B:
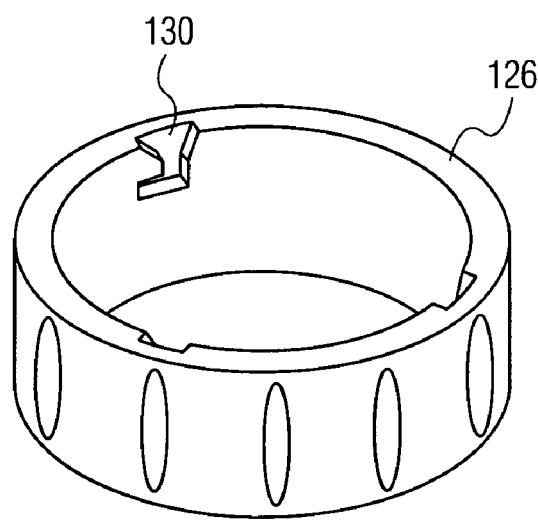
FIG. 9B is a schematic diagram showing in more detail a portion of the structure of FIG. 9A.

FIGS. 8A and 8B show another embodiment of the interface structure. It also includes a head portion 100 with protrusions 102 extending outwardly from the sides thereof, near the lower end thereof. The lower surface 104 of head portion 100 is configured to mate with the upper surface 106 of handle portion 108, with O ring 110 providing a fluid-tight connection between the two. Again, only one supply line 112 (with head and handle portions in registry) is shown for illustration.

A ring member 114 connects/locks the handle to the head. The ring 114 is connected to the handle portion by protrusions on the handle and matching cavities in the inner surface of the ring member 114. The inner surface of ring member 114 also includes spaced bayonet slots 115 which mate with the protrusions 102 on the head. In use, the head portion is moved into the ring by aligning protrusions 102 with the upper portions of slots 115, moving the head slightly toward the handle, and then rotating the ring, locking the head to the handle. The head is removed by oppositely rotating the ring fully in a counterclockwise direction, and then lifting the head away from the handle.

FIGS. 9A, 9B and 10A 10D show a variation of the structure of FIGS. 8A and 8B, comprising a handle 122, a head 124, a connecting ring 126 and an O ring seal 128. Again, only one supply line connection 129 (portions thereof in head and handle in registry) is shown for simplicity of illustration. Ring 126 mates with the handle by a spaced protrusions/cavities arrangement. Ring 126 has a plurality of inner surface slots 130, shown most clearly in FIGS. 10A 10D, extending from the top edge thereof, with the ring being spring-loaded by means of spring 132.

Figure 10A:
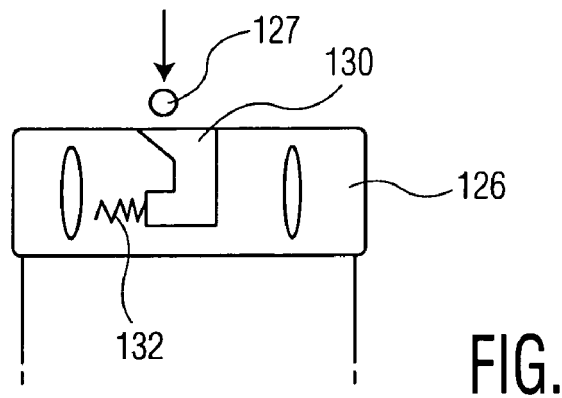
FIGS. 10A to 10D are a series of schematic views showing the positioning of a head portion onto a handle portion with the structure of FIGS. 9A and 9B.
Figure 10B:
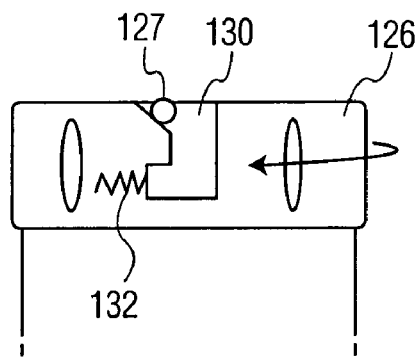
Figure 10C:
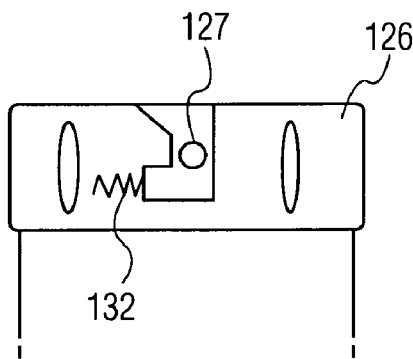
Figure 10D:
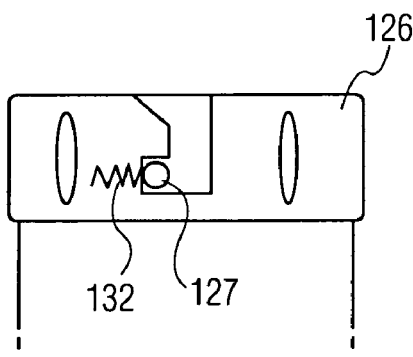

In use, head 124 is inserted into the ring at the top thereof, with the spaced protrusions 127 on the outer surface of the head entering the slots 130 at the tops thereof. As the head is pushed down toward the handle, the configuration of the slot is such as to force ring 126 to rotate clockwise against the action of the spring 132 (FIG. 10C), until the protrusions are at the bottom of the slots, level with a horizontal portion of the slots, at which point spring 132 rotates ring 126 back counterclockwise, with the protrusions coming against the ends of the horizontal portions of the slots, resulting in a locking of the head to the handle. To remove the head, the ring is rotated counterclockwise against the spring until the protrusions encounter the opposing end of the horizontal portion of the slots, at which point the head can be lifted away from the ring and hence the handle portion as well.

Figure 11A:
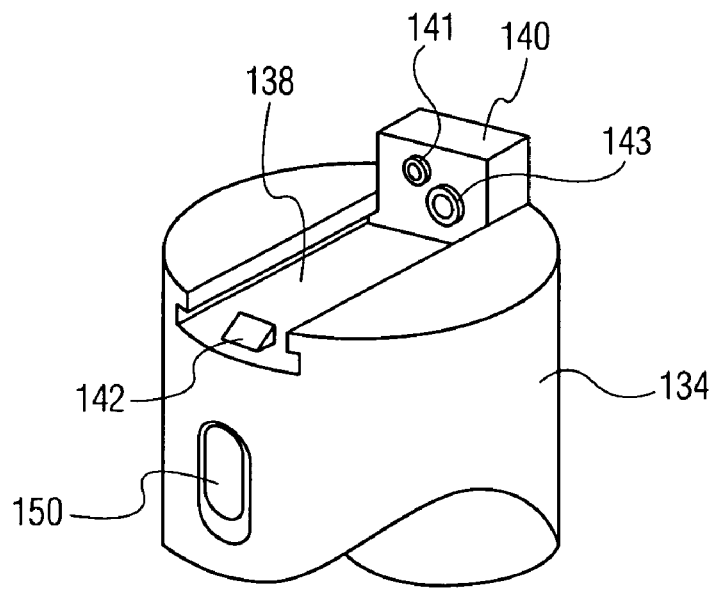
FIGS. 11A and 11B are schematic and cross-sectional views, respectively, of another embodiment of the interface structure.
Figure 11B:
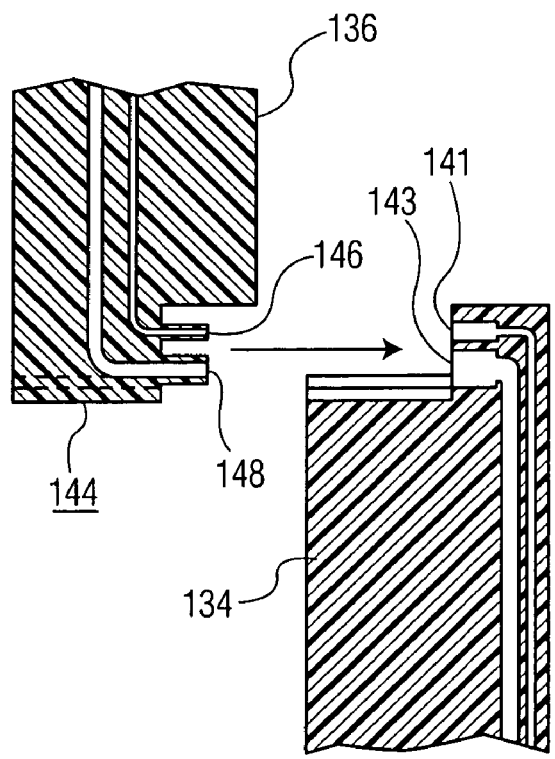

FIGS. 11A and 11B show a different interface arrangement. The system includes a handle 134 and a head 136. In the top surface of handle 134 is a T shaped slot 138, at the end of which is a connector block 140 with two openings 141, 143 therein which connect to the gas and liquid supply lines in the handle. A pin member 142 extends upwardly in the T shaped slot 138, spring-loaded in the raised position, as shown in FIG. 11A. The lower surface 144 of head 136 is configured to mate with the T shaped slot 138 and also includes extending connectors 146 and 148 which are configured to mate in a fluid-tight relationship with the openings 141, 143 in the connector block 140.

Pin member 142 in operation locks the head to the handle, as the head portion is slid into the T shaped slot, mating with connector block 140. When the head is to be removed, button 150 is operated downwardly, moving pin 142 downwardly out of engagement with the head, permitting the head to be slid off and away from the handle.

Figure 12A:
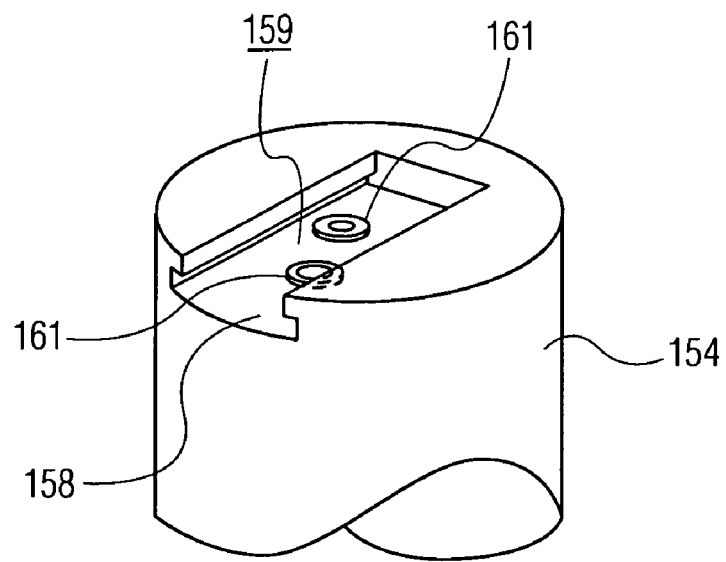
FIGS. 12A and 12B are schematic and cross-sectional views, respectively, of yet another embodiment of the interface structure.
Figure 12B:
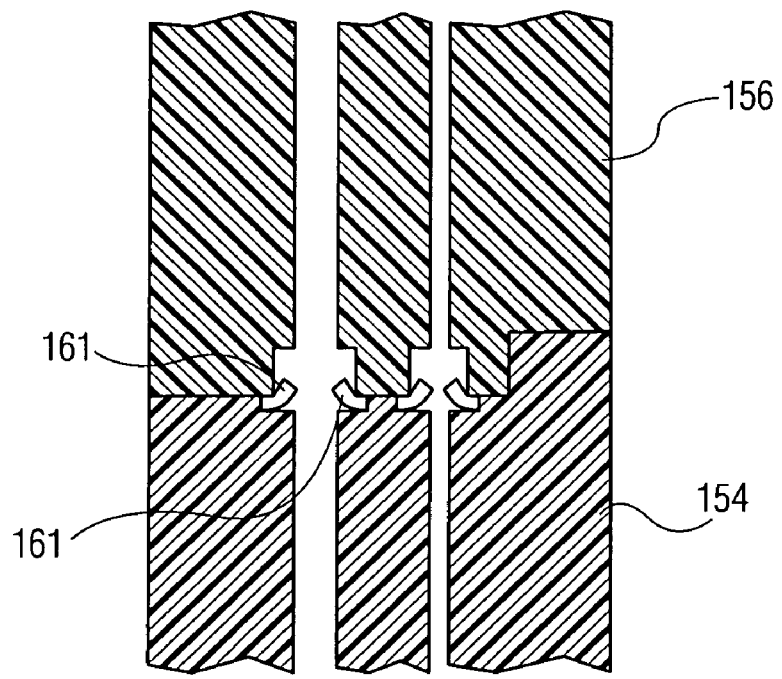

FIGS. 12A and 12B show a variation of the embodiment of FIGS. 11A and 11B. This embodiment includes a handle portion 154 and a head portion 156. The head portion engages the handle portion by a T shaped slot 158 in the upper surface of handle 154 and a mating portion in the lower surface of head 156. Liquid and gas lines extend upwardly in the handle, terminating at surface 159 of the T shaped slot with flexible annular seal elements 161. Flexible seal elements 161 are designed such that as head 156 is moved onto handle 154, the inner portions of the seal elements lift up, sealing against the edge of liquid and gas lines in the head which are in registry with the liquid and gas lines in the handle.

Figure 13A:
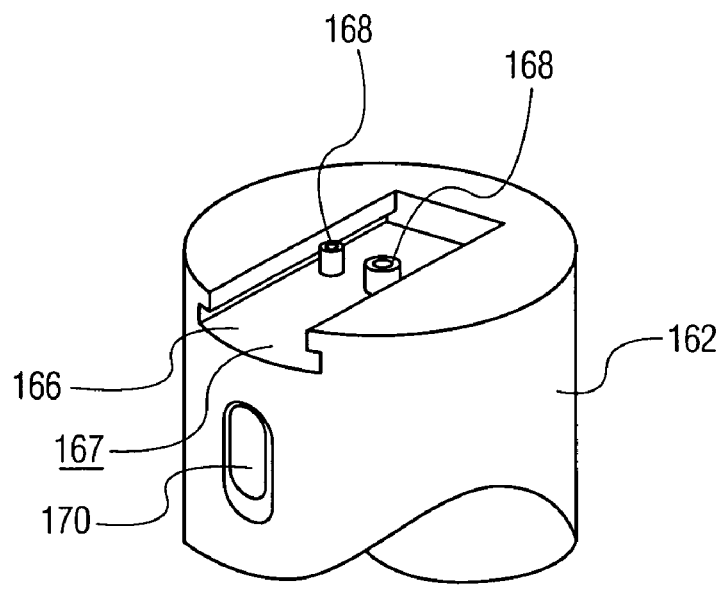
FIGS. 13A and 13B are schematic and cross-sectional views, respectively, of another embodiment of the interface structure.
Figure 13B:
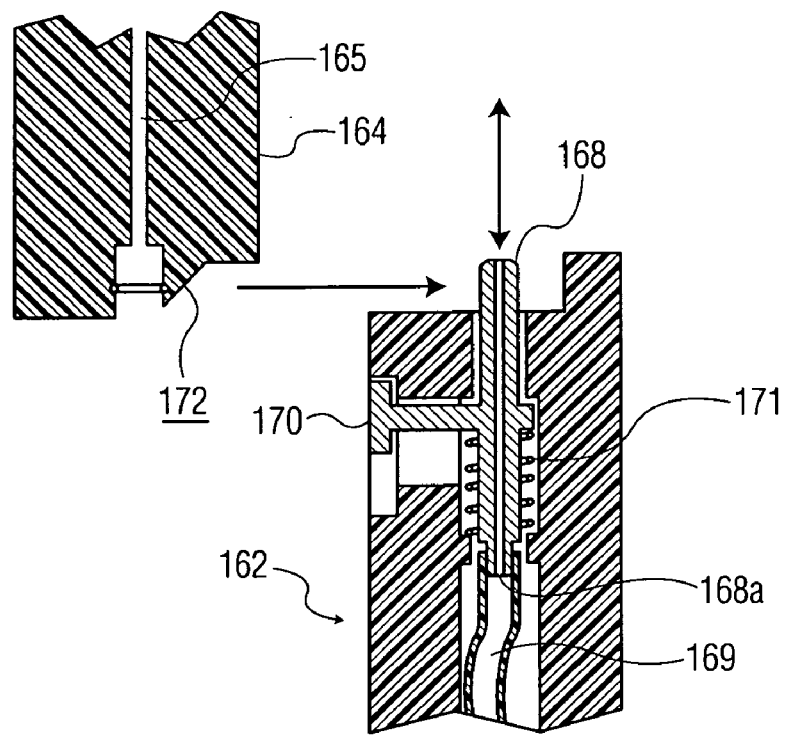

FIGS. 13A and 13B show a further variation of the arrangements of FIGS. 11A, 11B and 12A and 12B. FIGS. 13A, 13B include a handle 162 and a head 164. Handle 162 has a T shaped slot 166 in the upper surface thereof, and two spring-loaded connectors 168 which extend upwardly above the surface 167 of T shaped slot 166 in their unloaded condition. The lower edges 168a of the connectors, located within the handle, are secured to flexible fluid and gas lines 169 (one is hidden), as shown in FIG. 13B. A button 170 extends from the connectors 168 to the outer surface of handle 162.

The head 164 includes liquid and gas lines 165 (only one is shown) which open onto a lower surface 172 of head 164 and receive connectors 168.

In use, head 164 is slid onto the handle, with the lower surface 172 of the head being configured to force the spring-loaded connectors 168 downwardly against their spring bias until the head is fully onto the handle, where the connectors 168 are in registry with lines 165 in the head, at which point the connectors 168 spring back under the action of spring 171 to a fluid-tight connection with lines 165. To release/remove the head from the handle, button 170 is pushed downwardly, releasing the connectors 168 from the corresponding lines 165 in the head 164, and the head is slid away from the handle.

Figure 14A:
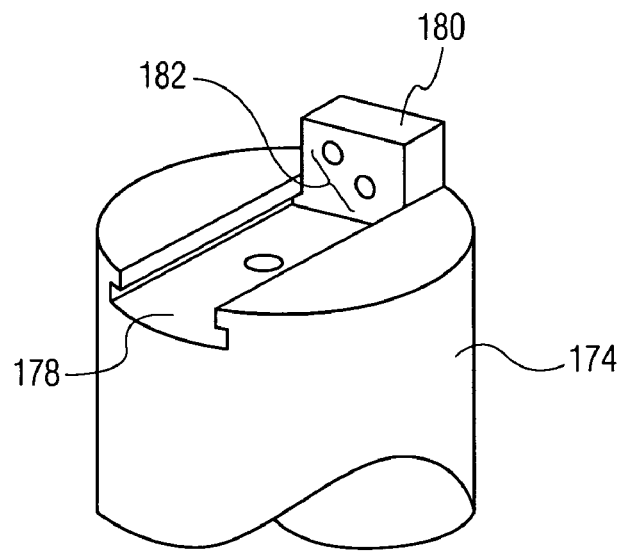
FIGS. 14A and 14B are schematic and cross-sectional views, respectively, of another embodiment of the interface structure.
Figure 14B:
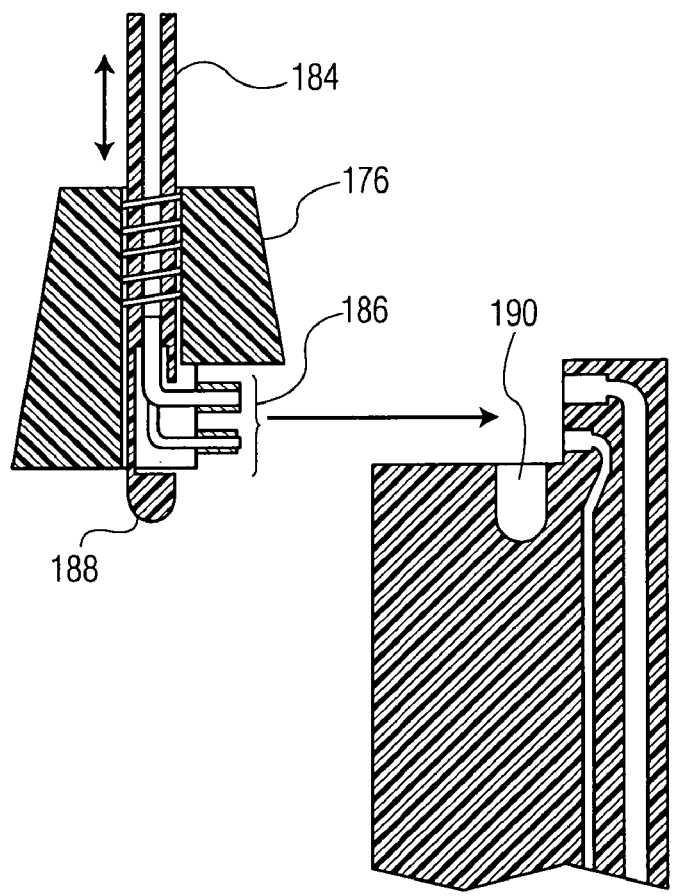

FIGS. 14A and 14B show a further variation involving a handle 174 with a T shaped slot 178 in the upper surface thereof and a head portion 176 having a matching lower surface for engagement therewith. At the rear of T shaped slot 178 is a connector block 180 which has openings 182 therein which connect with the liquid and gas lines in the handle.

The head 176 includes a spring-loaded tube 184 within which are liquid and gas lines which terminate in fluid and gas connectors 186, which mate with openings 182 in the connector block 180 in a fluid-tight relationship when the head is connected to the handle. To engage the head to the handle, tube 184 is pulled upwardly, such that a bulbous portion 188 at the bottom of tube 184 is retracted fully into the head. The head is then slid fully onto the handle, and the tube 184 released, with bulb portion 188 then mating with a matching cavity 190 in the top surface of the handle, locking the head onto the handle. To release/remove the head, the tube 184 is raised, and the head is then slid away from the handle.

Figure 15A:
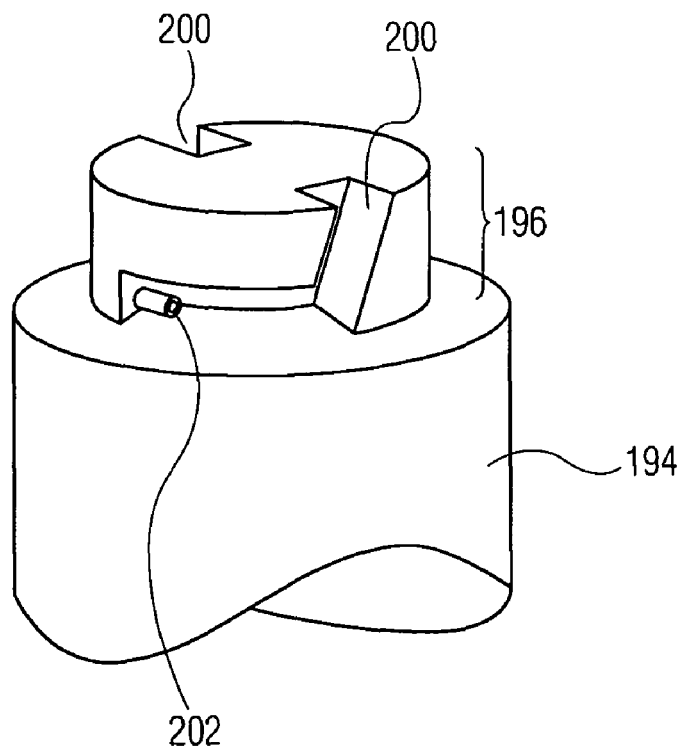
FIGS. 15A and 15B are schematic and cross-sectional views, respectively, of still another embodiment of the interface structure.
Figure 15B:
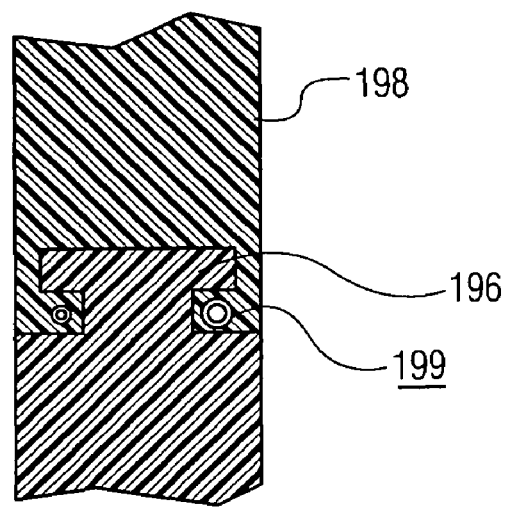

FIGS. 15A and 15B show another embodiment of the head/handle interface, involving a handle 194 with a raised central portion 196 which is generally circular in configuration. The lower surface 199 of the head 198 has a mating mirror image configuration. The raised central portion 196 includes two opposing bayonet-type slots 200 at the end of which are hollow connectors 202 which connect with the gas and liquid lines in the handle. The connectors 202 mate with matching openings in the lower portion of head 198 in a fluid-tight relationship when the head is positioned onto the handle and rotated to lock the head to the handle. The openings in the head connect with liquid and gas lines (not shown) in the head.

Figure 16A:
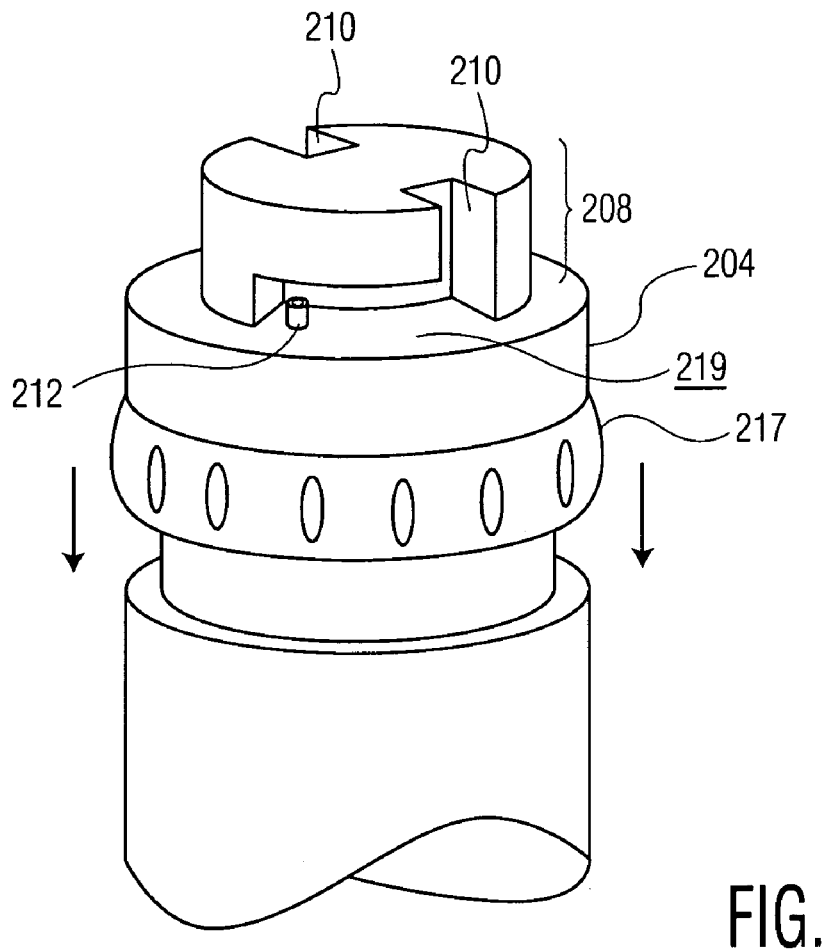
FIGS. 16A and 16B are schematic and cross-sectional views, respectively, of a further embodiment of the interface structure.
Figure 16B:
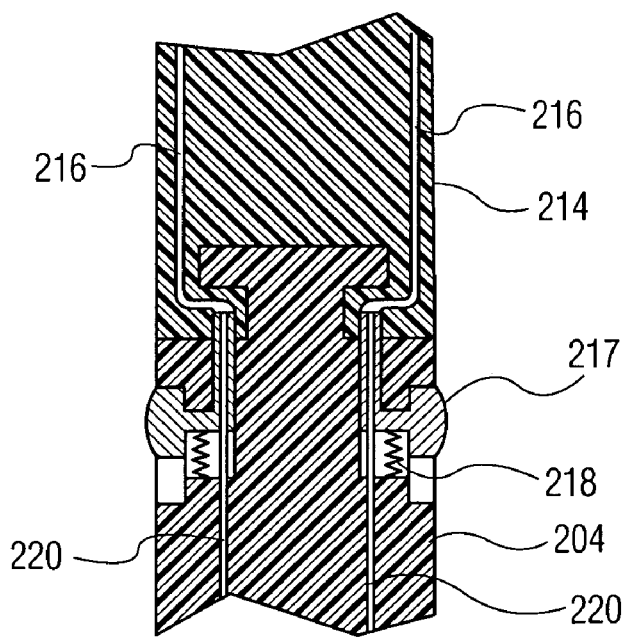

FIGS. 16A and 16B show a variation of the embodiment of FIGS. 15A and 15B, comprising a handle portion 204, with a raised central portion 208 having opposed bayonet slots 210 therein. Gas and liquid hollow connectors 212 extend upwardly vertically near the end of the bayonet slots. Head 214 includes a mating lower surface configuration, with gas and liquid lines 216 which are in registry with and connect to connectors 212 from the handle in a fluid-tight relationship when the head is operatively positioned on the handle.

The interface system includes a spring-loaded ring 217 connected internally to the two fluid connectors 212, which in turn are connected to the gas and liquid lines 220 in the handle. The ring 217 is biased by a spring 218 in the up position, where the connectors extend above surface 219 of the handle. When the ring 217 is moved downwardly, connectors 212 are moved down below surface 219 and the head is then inserted onto the handle and rotated in the bayonet slots, locking the head to the handle. Ring 217 is then released, and the action of spring 218 forces connectors 212 upwardly, engaging the gas and liquid lines 216 in the head 214 in a fluid-tight relationship. To release the head, ring 217 is moved downwardly, disengaging the connectors 212 from the gas and liquid lines in the head. The head may then be rotated and removed from the handle.

Figure 17:
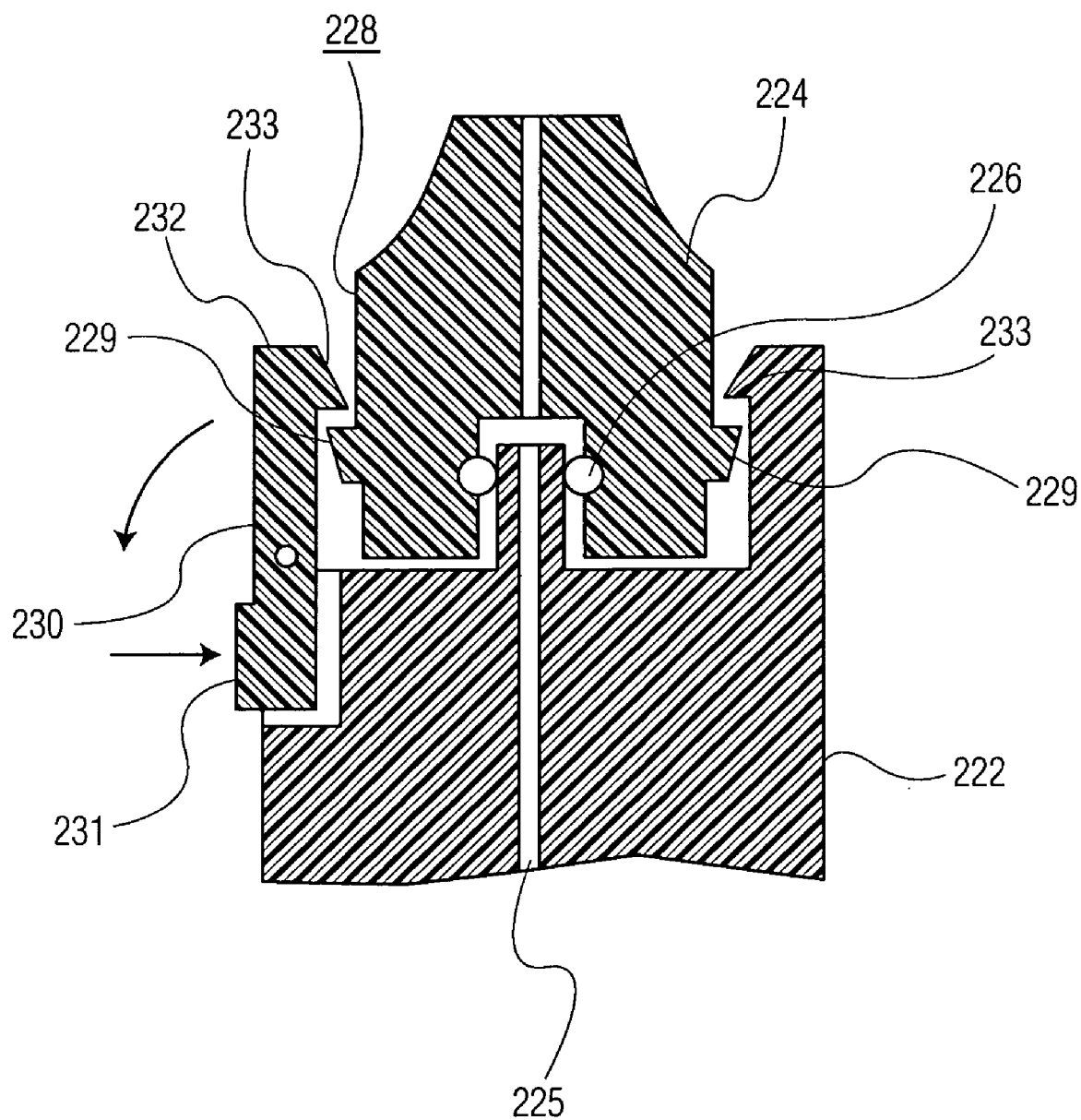
FIG. 17 is a cross-sectional view of another embodiment of the interface structure.

FIG. 17 shows an interface arrangement involving a handle 222 and a head 224, with an O ring 226 providing a seal between the head and handle portions. Gas and liquid lines 225 (only one is shown) from the handle portion are in registry with gas and liquid lines in the head when the head is operatively positioned onto the handle. Extending from the outer surface 228 of head 224 are projections 229. Pivotally connected to handle 222 is an elastic connecting member 230 which, when pushed inwardly at a lower end 231 thereof, results in the upper end 232 thereof moving away from the head portion.

The upper portion of the elastic member 230 includes a ridge 233 which mates with projections 229 and holds the head onto the handle portion. Ridge portions 233 and projections 228 have configurations such that the action of pushing the head onto the handle initially forces the upper portion of elastic member 230 outwardly, until the projections 229 can pass by the ridges 233, at which point the upper portion of the elastic member snaps back, capturing the head in relationship to the handle. When head 224 is to be removed from handle 222, the lower portion 231 of the elastic member 230 is pushed inwardly, forcing the upper portion out of the way of its mating projection, permitting the head to be removed.

Figure 18C:
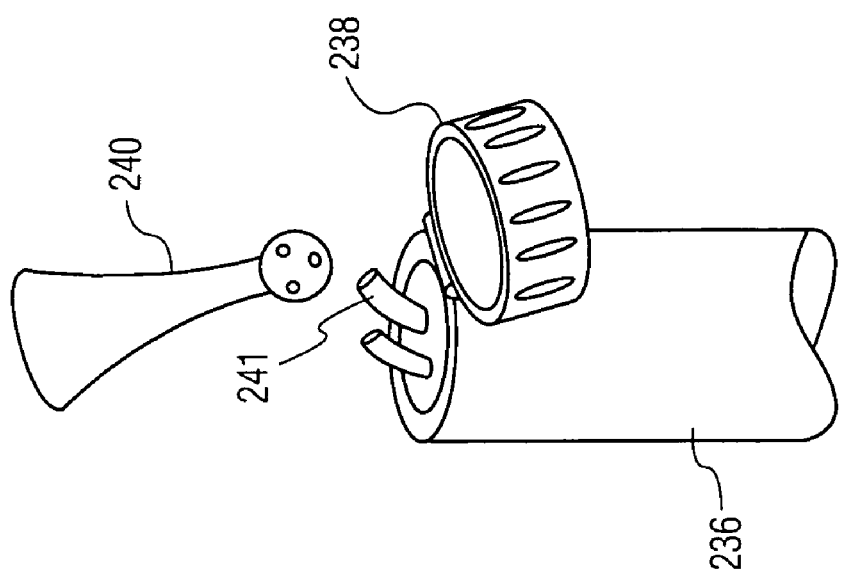
FIGS. 18A to 18C are schematic views of another embodiment of the interface structure.
Figure 18B:
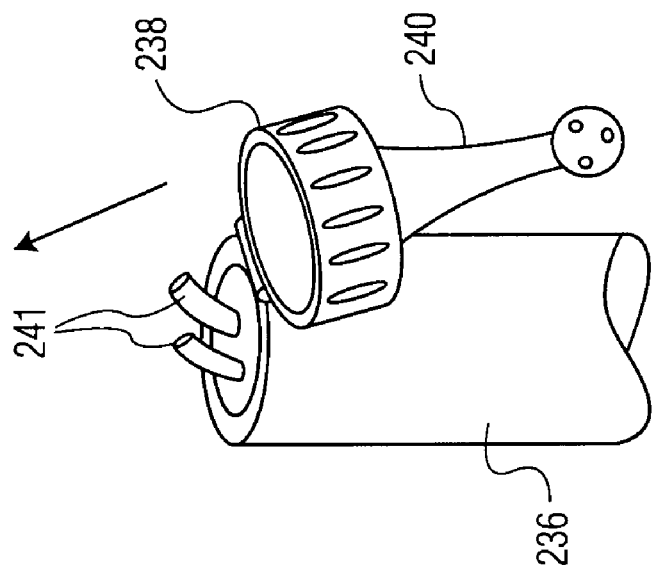
Figure 18A:
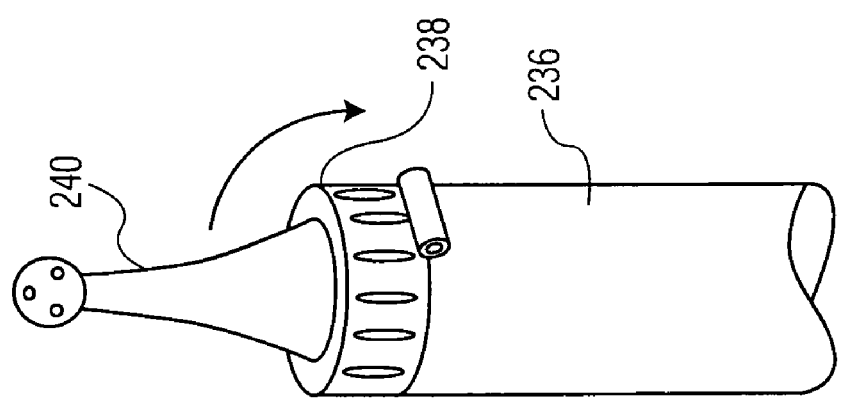

FIGS. 18A 18C show an interface arrangement by which a handle 236 has a ring member 238 hingedly connected thereto, with a head portion 240 being removable from the ring. Handle 236 has gas and liquid lines 241 extending from the upper surface thereof, which mate with corresponding gas and fluid lines in the head portion when the head is operatively positioned on the handle.

Figure 19:
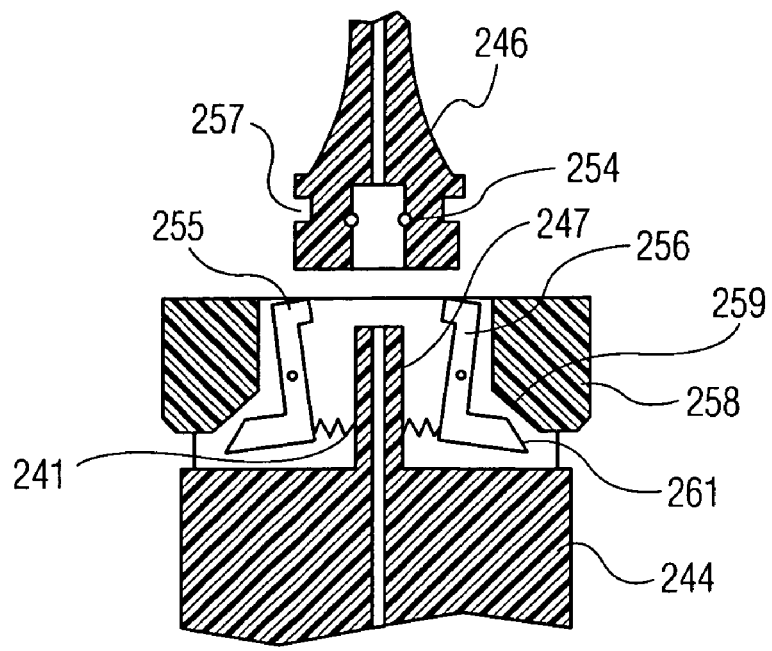
FIG. 19 is a cross-sectional view of yet another embodiment of the interface structure.

FIG. 19 shows another interface embodiment which includes a handle 244 and a head 246, with the upper surface of handle 244 having a raised center portion 247 through which gas and liquid lines extend, and which mates with a corresponding lower surface of head 246. An O ring 254 provides a fluid-tight connection between the head and handle, with the gas and liquid lines in the handle being in registry with the gas and liquid lines in the head, when the head is operatively positioned on the handle.

The interface includes two opposing spring-loaded hooks 255 and 256 which are biased in a closed position (toward each other). A ring member 258 has a lower internal edge 259 configuration which mates with the outer lower edge 261 of the hooks in such a manner that when the ring 258 is moved downwardly toward the handle, the hooks 255 and 256 are forced apart, permitting convenient insertion (or removal) of the head 246 relative to handle 244.

When the head is positioned on the handle, the ring is released and the action of the spring 241 forces the upper ends of hooks 254, 256 inwardly into engagement with corresponding slots 257 in the head, thereby holding the head tightly to the handle. The head is removed by pushing the ring 258 downwardly, forcing the hooks 255, 256 out of engagement with the head, against the action of the spring 241, permitting the head to be easily removed from the handle.

FIGS. 20A and 20B show a still further embodiment, involving a handle 262 and a head 264. Rotatably mounted for a small degree of rotation in handle 262 is a connector 266, which includes upstanding connector portions 263, 265 through which gas and liquid lines extend. Flexible gas and liquid lines 267, 269 are connected to the lower end of the connector 266. The lower surface of the head 264 is configured to mate with the upstanding portions 263, 265, sealed by separate O rings 268 and 270. When the head is operatively connected to the handle, the flexible lines 267, 269 are in registry with corresponding gas and liquid lines in head 264.

Projections 271 from the side surface of head 264 mate with bayonet slots 272 in the inner surface 273 of handle 262. The head is fitted onto the handle portion by engaging the projections 271 with the upper portion of the slots 272 and pushing downwardly, until the head is fully onto the handle portion, including mating with connectors 263, 265. The head 264 is then rotated a small amount, rotating connector 266 therewith, and locking the head to the handle. The head is removed by rotating the head in the opposite direction and then pulling the head off of the connector 266 and the handle.

FIG. 21 is the reverse arrangement of that shown in FIGS. 20A and 20B, including a handle 280 and a head 284, with a connector 286 being rotatably mounted in head 284. Connector 286 is adapted to mate with upstanding elements 288 and 290 in the handle. O rings 292 provide a seal between the head and handle. Projections 294 from the side surface of head 284 mate with slots in the inner surface of handle 280 to lock the head to the handle. To remove the head, it is simply rotated in the opposite direction and then lifted away from the handle.

Accordingly, a head/handle interface structure for a gas-assisted droplet jet system for cleaning teeth having a number of different embodiments has been shown and described. In all of the embodiments, a single action by the user in connecting/disconnecting the head from the handle results in disconnecting both the gas and liquid lines between the head and the handle portions of the droplet jet system. Typically, the interface is arranged so that the gas line in the handle can only fit to the gas line in the head, and the liquid line in the handle can only fit to the liquid line in the head. The system, including all the various embodiments, is safe and convenient to use. Valve controls can be provided on the embodiments, to ensure that the fluid and gas lines are blocked when the head is disconnected from the handle. Further, the arrangements are designed to withstand a pressure of 8 Bar, although this can vary from application to application.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. An interface structure for connecting a handle portion (12) of a droplet jet teeth cleaning system to a head assembly portion (18), comprising:
a handle portion containing a source of fluid from which droplets may be produced in the head portion and a source of gas for accelerating the resulting droplets to a desired velocity, including separate supply lines (14, 16) for liquid and gas in the handle;
a head assembly having separate supply lines (28, 30) for liquid and gas and an assembly for accelerating the liquid droplets out of the head assembly using gas from the gas supply line therein, wherein the handle liquid and handle gas supply lines, respectively, are arranged to align only with the head liquid and head gas supply lines when the head is operatively positioned on the handle; and
a sealing interface arrangement (15,17, 20, 21, 22) for sealing the head gas line directly to the handle gas line and the head liquid line directly to the handle liquid line, respectively, when the head portion is operatively positioned on the handle portion, wherein the handle and head portions are so configured, with or without a locking member, that the head and handle portions can be locked together with the respective gas lines and the respective fluid lines being in a directly sealed relationship and such that as the head portion is positioned onto the handle portion, the respective liquid lines and gas lines in the head and handle come into registry as a result.

2. The system of claim 1, including a locking member (36) which comprises a ring assembly which in one position locks the head portion to the handle portion, and in another position permits the head portion to be positioned onto and removed from the handle portion.

3. The system of claim 2, wherein the ring assembly and the handle portion include a mating bayonet connection (102, 115) for locking and unlocking the head portion to the handle portion.

4. The system of claim 1, wherein the upper surface of the handle portion is configured to mate with the lower surface of the head portion with a bayonet connection, as the head portion is rotated in one direction relative to the handle portion to lock the head portion to the handle portion and in the opposing direction to release the head portion from the handle portion, wherein when the head portion is locked to the handle portion, the gas lines in the head and handle portions and the liquid lines in the head and handle portion, respectively, mate in a fluid-tight relationship.

5. The system of claim 2, wherein the ring assembly threadably mates with the handle portion for locking and unlocking the head portion to the handle portion.

6. The system of claim 1, wherein the upper surface of the handle portion (134) includes a T-shaped slot (138) and the lower surface (144) of the head portion (136) includes a mating portion for locking and unlocking the head portion to the handle portion.

7. The system of claim 6, wherein the handle portion includes a connector block (140), at the rear of the T-shaped slot, having openings (141, 143) therein which connect to the gas and fluid lines in the handle portion, and wherein the head portion includes mating connector elements (146, 148) which fit into the openings in the connector block in a fluid-tight relationship when the head is operatively positioned onto the handle, the mating connector elements being in fluid connection with the gas and liquid lines in the head portion.

8. The system of claim 7, including a spring-loaded retractable pin member (142) for holding the head portion onto the handle portion, and for preventing the head portion from being removed when the pin is in its nonretracted position.

9. The system of claim 6, wherein the handle portion includes spring-loaded, retractable connectors (168) which extend upwardly into the T-shaped slot (167) and mate with corresponding connections in the head portion in a fluid-tight relationship when the head is operatively positioned on the handle, the system further including a control member (170) which when operated moves the retractable connectors downwardly away from engagement with the corresponding connectors on the head portion, permitting the head portion to be removed from or inserted on the handle portion.

10. The system of claim 1, wherein the head portion (62) has elastic ears (63, 64) extending upwardly from a lower portion thereof, wherein in an inward position of the elastic ears, the head portion may be moved onto and away from the handle portion (70), and wherein in a spread position of the elastic ears, projections (76) on an exterior surface of the elastic member engage corresponding slots (78) in an upper portion of the handle to lock the head portion to the handle portion.

11. The system of claim 1, including a ring assembly (126) which is spring-loaded (132) and rotatably mounted on the handle portion (172) and includes a plurality of bayonet slots (130) in an inner surface thereof, configured such that as the head portion is moved onto the head portion, projections (127) on the head portion force the ring assembly to rotate against the spring action until the projections reach a bottom of the slots, at which point the spring moves the ring portion in the other direction, with the projections being captured in another portion of the slots to lock the head portion to the handle portion.

12. A system of claim 1, further including a ring assembly (258) and opposing spring-loaded hook members (255, 256) which are adapted to engage with corresponding slots (257) in the head portion (246), wherein the ring assembly is so configured relative to the spring-loaded hook members, that temporarily moving the ring assembly toward the handle forces an upper portion of the hook member outwardly, permitting the head portion to be inserted or removed from the handle portion, and when released, permitting the hook members to engage the head portion in a locking arrangement.

13. The system of claim 1, wherein one of the head (264) and handle (262) portions has a connector assembly (266, 286) rotatably mounted therein, the connector assembly having connector portions (263, 265) receiving gas and fluid lines in the head or handle portion in which it is located, and further adapted to connect in a fluid-tight relationship with corresponding gas and fluid lines in the other of the head and handle portions, wherein the head portion has projections (271, 294) which engage with mating slots (272) in the handle portion, permitting rotation of the head relative to the handle and locking of the head portion to the handle portion.

14. The system of claim 1, including a ring member (238) which is hingedly secured to the handle member (236), and wherein the head portion (240) is removably secured to the ring member.

15. The system of claim 1, including a plurality of elastic legs (90) positioned in the upper surface of the handle portion (84) and extending upwardly thereof and a ring assembly (94) which is threadably mounted on the handle portion, such that when the ring assembly is turned in the direction, upper portions of the elastic legs are forced against a lower part (93)

of a head portion which is positioned on the handle portion, thereby locking the head portion to the handle portion, and such that when the ring assembly is turned in an opposing direction, the upper portions of the elastic member are released from contact with the head portion, permitting the head portion to be removed from the handle portion.

16. The system of claim 1, wherein the gas and liquid lines are physically separate from and independent of each other in both the handle and the head portions.

17. The system of claim 1, wherein the gas and liquid lines are in a concentric coaxial relationship (42, 44) in both the handle and the head portion.

18. The system of claim 1, including control means (58) for preventing gas and liquid from escaping from the supply lines in the handle portion when the head portion is removed from the handle.

19. The system of claim 18, wherein the control means includes an electrical switch (57) and mechanical shutoff valves (58) for the gas and liquid lines.

20. The system of claim 18, wherein the control means includes a pin/ball assembly (60, 61) for blocking the supply lines in the handle when the head portion is removed from the handle portion.

21. The system of claim 1, including a locking assembly (59) for locking the head to the handle when the system is pressurized.

22. An interface structure for connecting a handle portion (12) of a droplet jet teeth cleaning system to a head assembly portion (18), comprising:

a handle portion and a head portion, the handle portion having a source of liquid from which droplets are produced in the head portion and a source of gas for accelerating the droplets in the head portion to a desired velocity for use in cleaning teeth, the handle portion including supply lines (14, 16) for the liquid and the gas, wherein an upper part of the handle portion is so configured, along with the liquid and gas lines therein, relative to a lower part of the head portion and the liquid and gas lines therein, that when the head portion is operatively positioned on the handle portion, a direct fluid-sealing relationship results between the respective gas lines of the handle and head, and the respective liquid lines of the handle and head, and wherein the connection/disconnection and direct sealing of the respective gas lines and the respective liquid lines occurs automatically when the head portion is operatively positioned on or removed from the handle portion, with or without a locking member.

* * * * *